(12) United States Patent
Wampler et al.

(10) Patent No.: US 6,485,490 B2
(45) Date of Patent: *Nov. 26, 2002

(54) RF BIPOLAR END EFFECTOR FOR USE IN ELECTROSURGICAL INSTRUMENTS

(75) Inventors: Scott D. Wampler, West Chester, OH (US); William L. Collins, Jr., Cincinnati, OH (US); David C. Yates, West Chester, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 30 days.

This patent is subject to a terminal disclaimer.

(21) Appl. No.: 09/765,250

(22) Filed: Jan. 18, 2001

(65) Prior Publication Data

US 2001/0001820 A1 May 24, 2001

Related U.S. Application Data

(63) Continuation of application No. 09/241,575, filed on Feb. 2, 1999, now Pat. No. 6,296,640.
(60) Provisional application No. 60/073,890, filed on Feb. 6, 1998.

(51) Int. Cl.[7] ............................................... A61B 18/18
(52) U.S. Cl. .......................................... 606/48; 606/50
(58) Field of Search ............................. 606/41, 42, 45, 606/48–52, 206

(56) References Cited

U.S. PATENT DOCUMENTS

| | | | |
|---|---|---|---|
| 2,031,682 A | 2/1936 | Wappler et al. | |
| 5,080,660 A | 1/1992 | Buelna | |
| 5,207,691 A | 5/1993 | Nardella | |
| 5,258,006 A | 11/1993 | Rydell et al. | |
| 5,267,998 A | 12/1993 | Hagen | |
| 5,269,780 A | * 12/1993 | Roos | 606/42 |
| 5,366,476 A | 11/1994 | Noda | |
| 5,403,312 A | 4/1995 | Yates et al. | |
| 5,599,350 A | 2/1997 | Schulze et al. | |
| 5,688,270 A | 11/1997 | Yates et al. | |
| 5,693,051 A | 12/1997 | Schulze et al. | |
| 5,700,261 A | 12/1997 | Brinkerhoff | |
| 5,702,390 A | 12/1997 | Austin et al. | |
| 5,709,680 A | 1/1998 | Yates et al. | |
| 5,836,945 A | 11/1998 | Perkins | |
| 6,030,384 A | 2/2000 | Nezhat | |
| 6,165,175 A | 12/2000 | Wampler et al. | |

FOREIGN PATENT DOCUMENTS

WO    WO 98/36692    8/1998

* cited by examiner

*Primary Examiner*—Michael Peffley
(74) *Attorney, Agent, or Firm*—Verne E. Kreger (57) ABSTRACT

The present invention is directed to a bipolar electrosurgical end effector for use in medical instruments. A bipolar end effector according to the present invention includes a tissue slot and electrodes arranged on either side of the tissue slot. The opposing electrodes are electrically connected such that tissue passing through the slot is electrically treated with electrosurgical current passing laterally through the tissue. An end effector according to the present invention further includes a tissue separator arranged at the end of the slot to divide tissue as it is passed through the slot and after it is treated.

9 Claims, 8 Drawing Sheets

RF BIPOLAR END EFFECTOR FOR USE IN ELECTROSURGICAL INSTRUMENTS

This is a Continuation U.S. application Ser. No. 09/241,575 filed Feb. 2, 1999, now U.S. Pat. No. 6,296,640.

This application is related to the following co-pending patent applications: U.S. patent application Ser. No. 60/073,890 which is hereby incorporated herein by reference.

FIELD OF THE INVENTION

The present invention relates, in general, to an improved bipolar electrode configuration for use in bipolar electrosurgical instruments and, more particularly, to a bipolar electrode configuration including electrodes arranged around a fixed height tissue slot.

BACKGROUND OF THE INVENTION

RF (Radio Frequency) electricity has been used for decades to cauterize and coagulate tissue in surgical procedures. Devices used to apply RF energy to tissue fall generally into two categories: mono-polar and bipolar. Bipolar electrosurgical instruments incorporate both active and return electrodes into the surgical instrument, substantially restricting the flow of electric current to tissue that is placed between the electrodes. In mono-polar electrosurgical instruments, on the other hand, the return electrode is placed outside the patients body, on the patients skin. Thus, in a mono-polar electrosurgical instrument, current flows from the active or treatment electrode through the patients body to the return electrode. Both mono-polar and bipolar electrosurgical instruments rely, at least in part, upon resistance heating to treat (e.g. cauterize and/or cut) tissue. As current is passed through tissue, the electrical resistance of the tissue results in the dissipation of power in the form of heat. As the temperature of the tissue rises, its characteristics, including electrical resistance, change. When the tissue temperature reaches approximately 67–70 degrees C, coagulation begins. As additional energy is dissipated in the tissue collagen, which forms the backbone of the tissue matrix, continues to break down and "melt". Once the collagen begins to break down, the tissue begins to coagulate. When the collagen begins to break down, compression of the tissue will cause the compressed tissue layers to fuse, sealing adjacent blood vessels. When the tissue temperature reaches one hundred degrees C most fluids (including water) are driven off or evaporated from the tissue, desiccating the tissue and substantially increasing the electrical resistance of the tissue. The desiccated tissue may then be cut or separated with little effort. The rate at which energy is dissipated into tissue is dependent on many factors, including the electrical resistance of the tissue and the density of the electric current flowing through the tissue. Since electrosurgical instruments are generally designed to be used to treat a variety of tissue types, current density becomes an important design consideration, and, particularly in bipolar electrosurgical devices, current density is, for a particular tissue type, a function of the number, size, shape and placement of the device electrodes.

In many surgical applications, it is desirable to use bipolar electrical energy as a means of cutting and/or coagulating tissue. In bipolar electrosurgical instruments, it is generally desirable to ensure that the flow of electric current is confined to the tissue in the instrument and, to a significantly lesser extent to the tissue adjacent the instrument. Generally, in prior art bipolar electrosurgical instruments, these goals have been accomplished by designing an instrument which grasps or clamps the tissue prior to the application of electrosurgical energy. Such bipolar electrosurgical instruments are well know in the art and, in particular, many designs have been suggested for surgical instruments which coagulate tissue either prior to cutting the tissue or during the cutting process. In most of these instruments, the tissue is first grasped by jaws which apply pressure to the tissue prior to the application of electrosurgical energy. In such instruments, the grasping jaws either constitute or include the electrodes which supply the electrosurgical energy, although, in some designs, one or more of the electrodes may be incorporated into other elements of the instrument, including, for example, the cutting element. Thus, in such bipolar electrosurgical grasping instruments, the tissue being treated is first grasped, then electrosurgical energy is applied by the electrodes, then the tissue is cut or separated, and, finally, the tissue is released and the grasping instrument is moved to fresh tissue so that the process can be repeated. While this procedure is very effective in many surgical procedures, when working in certain types of tissue, such as mesentery tissue, it may become tedious to continuously grasp and release as the instrument is moved through the tissue. However, since tissue such as mesentery tissue is vascular and will bleed if the blood vessels are not adequately sealed, it is important to ensure that the blood in the tissue on either side of the cut line is thoroughly coagulated prior to separating the tissue. Further, since many modern surgical procedures are performed in very small spaces, there may not be sufficient room to use an instrument with jaws which must be opened after each application of electrosurgical energy.

It would, therefore, be advantageous to design a bipolar electrosurgical end effector adapted to coagulate and cut tissue while moving continuously through the tissue. It would further be advantageous to design a bipolar electrosurgical end effector adapted to coagulate and cut tissue, including vascular structures, while moving the end effector continuously through the tissue, wherein the coagulation region is substantially confined to the width of the jaw assembly. It would further be advantageous to design a bipolar electrosurgical end effector adapted to continuously receive, coagulate and divide the coagulated tissue as the electrosurgical end effector is moved through the tissue. It would further be advantageous to design a bipolar electrosurgical end effector adapted to continuously receive, coagulate and divide tissue wherein the electrosurgical current through the tissue in substantially self limiting.

SUMMARY OF THE INVENTION

The present invention is directed to a bipolar electrosurgical end effector for use in medical instruments. A bipolar end effector according to the present invention may include: a first tissue surface; a first elongated electrode on a first side of the first tissue surface; and a second elongated electrode on a second side of the first tissue surface. The second electrode is generally substantially parallel to the first electrode. A bipolar end effector according to the present invention further includes: a first central insulation region separating the first electrode from the second electrode; a tissue slot separating a second tissue surface from the first and second electrodes; and a tissue separator positioned between the first and second tissue surfaces. The tissue separator generally includes: a dividing edge at a distal end of the tissue separator; a first tissue guide extending proximally away from the dividing edge toward the first side; and a second tissue guide extending proximally away from the dividing edge toward the second side.

In a further embodiment of the present invention, a bipolar electrosurgical end effector may include: a first elongated electrode on a first side of the end effector; a second elongated electrode on the first side of the end effector, wherein the second electrode is substantially parallel to the first electrode; a third elongated electrode on a second side of the end effector, wherein the third electrode is substantially parallel to the first and second electrodes; and a fourth elongated electrode on the second side of the end effector, wherein the fourth elongated electrode is substantially parallel to the first, second and third electrodes. In this embodiment of the invention, a first central insulation region separates the first electrode from the third electrode and a second central insulation region separates the second electrode from the fourth electrode, and a tissue separator is positioned between the first and the second central insulation regions proximal to the distal end of the end effector. The tissue separator may include: a dividing edge at the distal end of the tissue separator; a first tissue surface extending proximally away from the dividing edge toward the first side of the end effector; and a second tissue surface extending proximally away from the dividing edge toward the second side of the end effector.

Further embodiments of the present invention may include a bipolar electrosurgical end effector wherein the tissue separator comprises a wedge shaped region and a bipolar electrosurgical end effector wherein the first electrode is positioned substantially directly opposite the third electrode and the second electrode is positioned substantially directly opposite the fourth electrode. In addition, embodiments of the present invention may include a bipolar electrosurgical end effector wherein the first and second electrodes are electrically connected and the second and third electrodes are electrically connected.

BRIEF DESCRIPTION OF THE DRAWINGS

The novel features of the invention are set forth with particularity in the appended claims. The invention itself, however, both as to organization and methods of operation, together with further objects and advantages thereof, may best be understood by reference to the following description, taken in conjunction with the accompanying drawings in which:

DETAILED DESCRIPTION OF THE INVENTION

Figure 1:
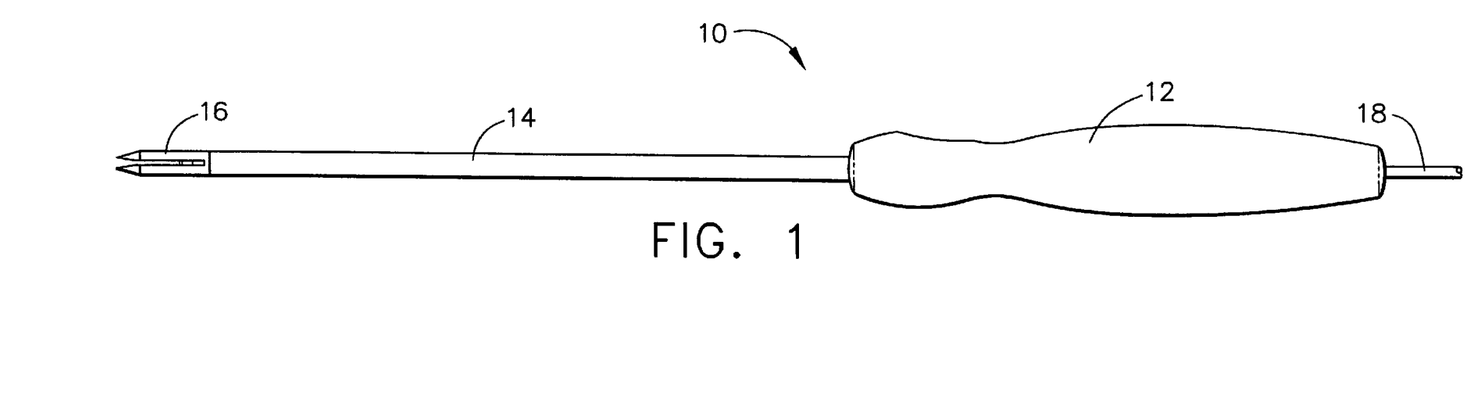
FIG. 1 is a side elevation view of a bipolar electrosurgical instrument according to the present invention.
Figure 2:
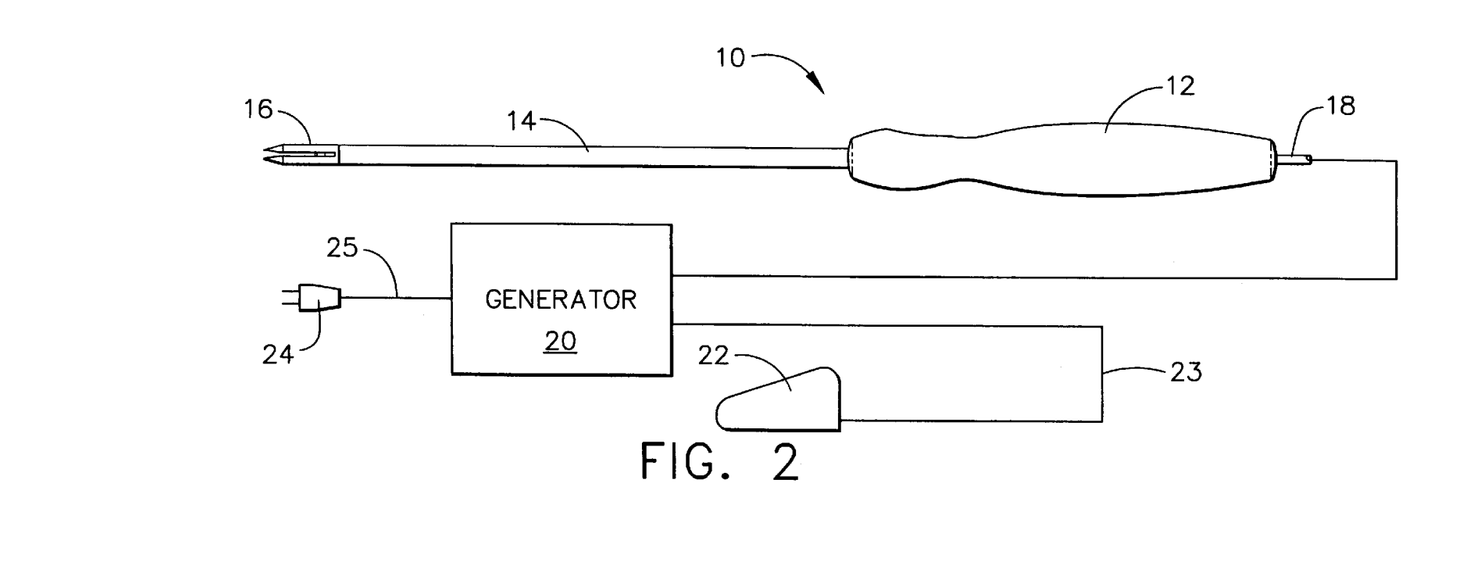
FIG. 2 is a side elevation view of the bipolar electrosurgical instrument illustrated in FIG. 1, including, in schematic form, an electrosurgical generator and foot switch.

FIG. 1 is a side elevation view of a bipolar electrosurgical instrument 10 according to the present invention. In the embodiment of the invention illustrated in FIG. 1, bipolar electrosurgical instrument 10 includes a handle 12, an extender tube 14, a jaw assembly 16 and a power cord 18. FIG. 2 is a side elevation view of bipolar electrosurgical instrument 10, including, in schematic form, an electrosurgical generator 20 and a foot switch 22. Electrosurgical generator 20 may be connected to ac wall plug 24 through generator power cord 25. Generator 20 may be, for example, an RF electrosurgery generator such as the generator available from ERBE Elektromedizin GmbH as model ICC 350. Electrosurgical generator 20 may be controlled and actuated by a conventional foot switch 22 which may be connected to generator 20 by foot switch cord 23. Electrosurgical generator 20 may be connected to bipolar electrosurgical instrument 10 by a power cord 18 which is adapted to carry bipolar electrosurgical energy to bipolar electrosurgical instrument 10.

Figures 3, 4:
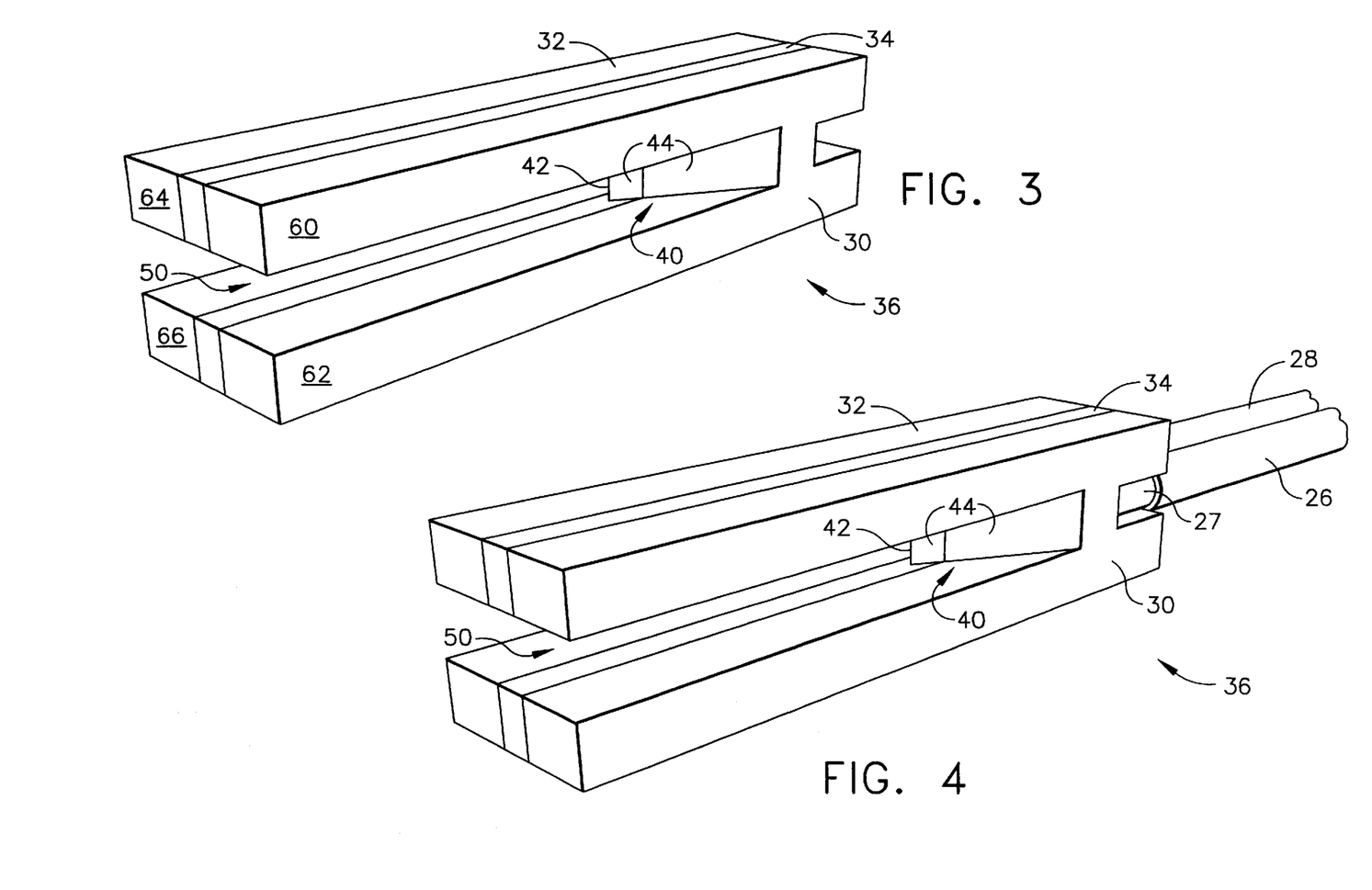
FIG. 3 is a perspective view of the end effector of the bipolar electrosurgical instrument illustrated in FIG. 1, including electrode assemblies, insulator assembly and a tissue separator according to the present invention.
FIG. 4 is a perspective view of the end effector illustrated in FIG. 3, including electrical conductors connected to the electrode assemblies.

FIG. 3 is a perspective view of the end effector 36 of the bipolar electrosurgical instrument 10, including first electrode assembly 30, second electrode assembly 32, central insulator assembly 34, tissue separator 40 and tissue slot 50. Tissue separator 40 may, as in the illustrated embodiment, preferably comprise a central wedge which includes a leading edge 42, a first wedge wall 44 and a second wedge wall 46 (which is visible in FIG. 10). While embodiments of tissue separators according to the present invention may include leading edges 42 which are surgically sharp, that is sharp enough to cut through healthy tissue without tearing the tissue, it may, in certain circumstances, be preferable to utilize a tissue separator wherein the leading edge 42 is surgically dull, that is too dull to readily cut healthy tissue but sharp enough to cut tissue which has been electrosurgically treated (e.g. desiccated tissue). FIG. 4 is a perspective view of end effector 36, including first electric wire 26 and second electric wire 28. First electrical wire 26 and second electrical wire 28 are electrically connected to power cord 18 and adapted to transmit electrosurgical energy from electrosurgical generator 20 to end effector 36. First electric wire 26 includes first electrical conductor 27 and second electrical wire 28 includes second electrical conductor 29 (which is visible in FIG. 5). First electrical conductor 27 is connected to first electrode assembly 30 by, for example, silver soldering first electrical conductor 27 to first electrode assembly 30. Second electrical conductor 29 is connected to second electrode assembly 32 by, for example, silver soldering second electrical conductor 29 to second electrode assembly 32. In the embodiment of end effector 36 illustrated in FIG. 3, first electrode assembly 30 includes first electrode 60 and second electrode 62 while second electrode assembly 32 includes third electrode 64 and fourth electrode 66.

Figure 5:
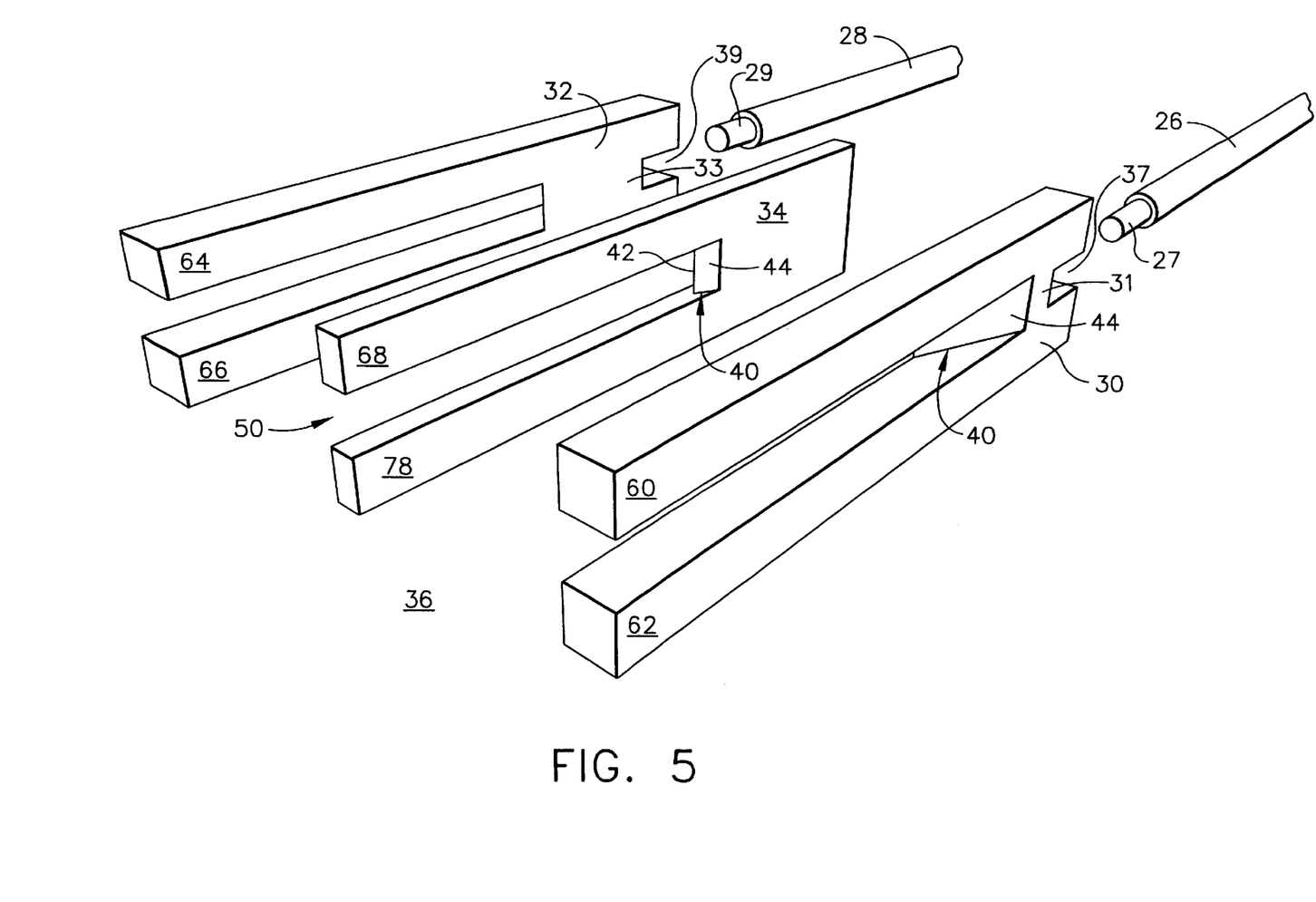
FIG. 5 is an exploded perspective view of the end effector illustrated in FIG. 4.

FIG. 5 is an exploded perspective view of end effector 36. In particular, FIG. 5 illustrates the structure of first electrode assembly 30, second electrode assembly 32 and central insulator assembly 34. In the embodiment of the invention illustrated in FIG. 5, first electrode assembly 30 includes first electrode 60 and second electrode 62 which are electrically and mechanically connected by first support member 31. Further, in the embodiment of the invention illustrated in FIG. 5, second electrode assembly 32 includes third electrode 64 and fourth electrode 66 which are electrically and mechanically connected by second support member 32. In this embodiment of the invention, first support member 31 includes at least a portion of first wedge wall 44 and second support member 33 includes at least a portion of second wedge wall 46. First electrode assembly 30 also includes a first conductor notch 37 and a second conductor notch 39 which are adapted to receive first electrical conductor 27 and second electrical conductor 29 respectively. First electrical conductor 27 is electrically and mechanically connected to first electrode assembly 30 by, for example, soldering first electrical conductor 27 into first conductor notch 37. Second electrical conductor 29 is electrically and mechanically connected to second electrode assembly 32 by, for example, soldering second electrical conductor 29 into second conductor notch 39. In the embodiment of FIG. 5, central insulator assembly 34, which may be formed of an electrically non-conductive material in substantially the same shape as first electrode assembly 30 and second electrode assembly 32, electrically isolates first electrode assembly 30 from second electrode assembly 32. Central electrode assembly 34 further includes a portion of first wedge wall 44, second wedge wall 46 and leading edge 42, which, in the embodiment illustrated in FIG. 5, are made of an electrically non-conductive material.

Figure 6:
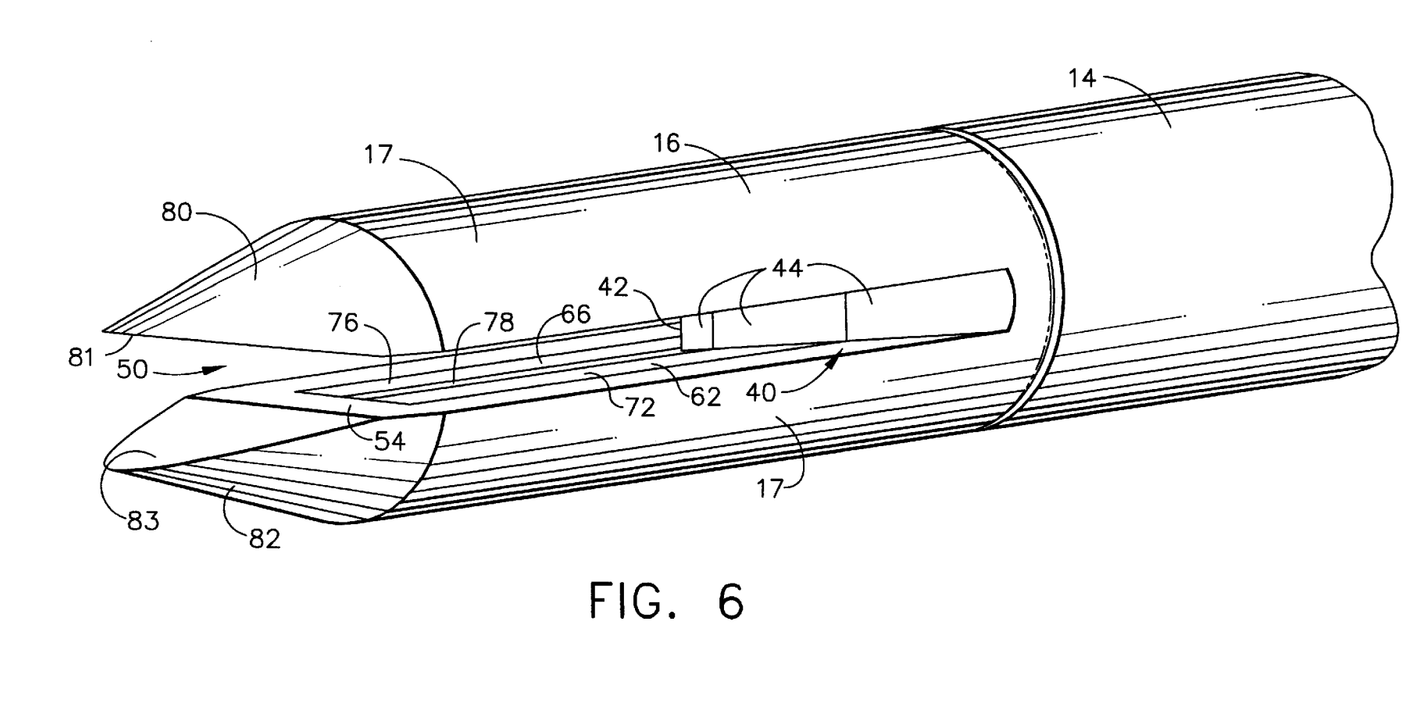
FIG. 6 is an enlarged isometric view of the jaw assembly at the distal end of the bipolar electrosurgical instrument illustrated in FIG. 1.

FIG. 6 is an enlarged isometric view of the distal end of bipolar electrosurgical instrument 10. First tissue surface 52 includes contact surface 70 of first electrode 60 and contact surface 74 of third electrode 64. First tissue surface 52 may further include a portion of first central insulator 68 which separates contact surface 70 from contact surface 74. In FIG. 6, tissue slot 50 is bounded by first tissue surface 52 (which is visible in FIG. 7) and second tissue surface 54. Second tissue surface 54 includes contact surface 72 of second electrode 62 and contact surface 76 of fourth electrode 66. Second tissue surface 54 may further include a portion of second central insulator 78 which separates contact surface 72 from contact surface 76, electrically isolating contact surface 72 from contact surface 76. Tissue separator 40, including leading edge 42, first wedge wall 44 and second wedge wall 46 forms at least a portion of the proximal end of tissue slot 50. An outer insulating shell 17 surrounds and isolates the elements of end effector 36, supporting end effector 36 and electrically isolating end effector 36 from tissue outside of tissue slot 50. First and second tissue surfaces 54 and 56 may also include at least a portion of insulating shell 17. Insulating shell 17 also includes upper dissector 80 and lower dissector 82 which each comprise partial cone shaped regions on either side of the distal end of tissue slot 50. Upper dissector 80 includes ramped surface 81 and lower dissector 82 includes ramped surface 83 which extend from the distal end of jaw assembly 16 to the distal opening of tissue slot 50.

Figure 7:
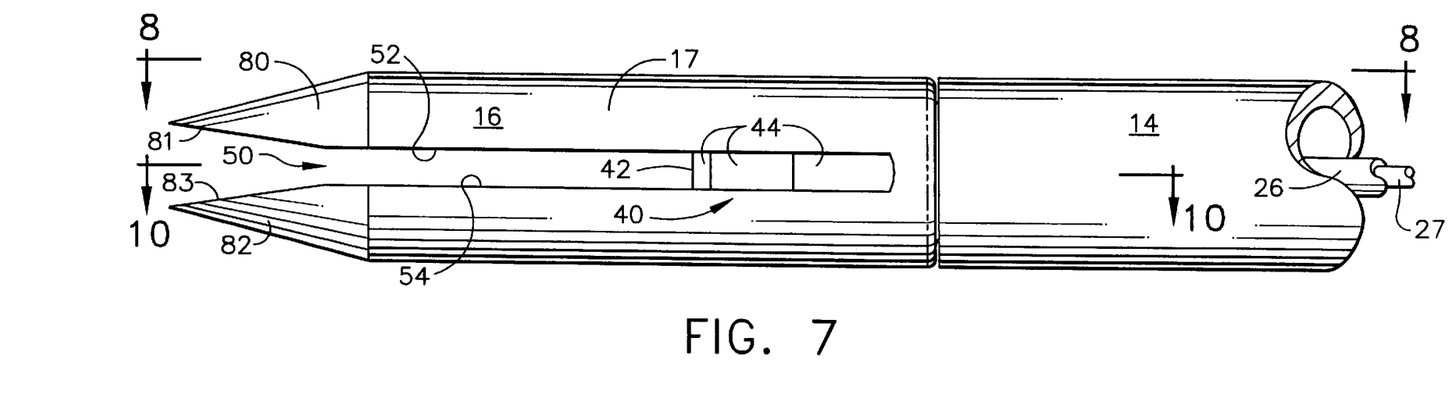
FIG. 7 is a side elevation view of the jaw assembly at the distal end of the bipolar electrosurgical instrument illustrated in FIG. 1.
Figure 8:
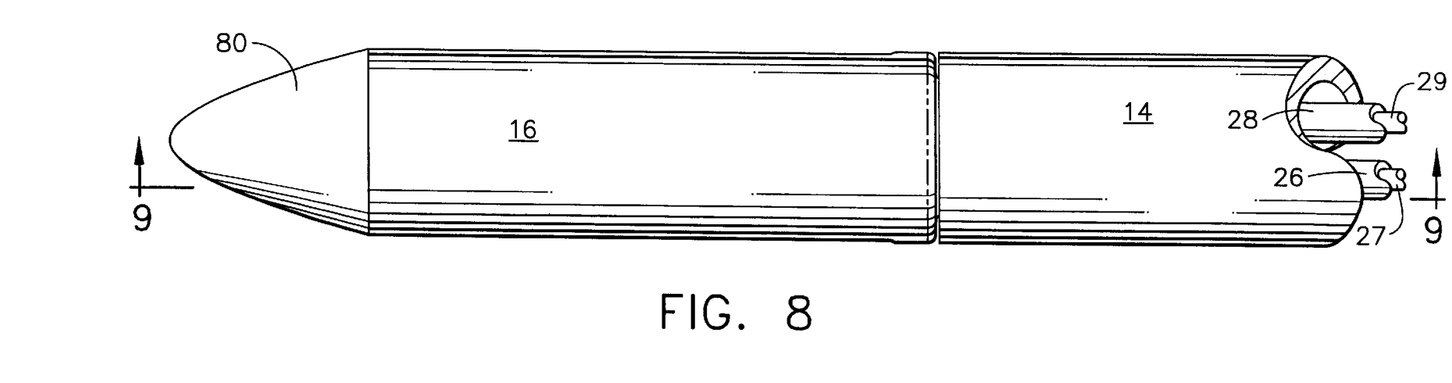
FIG. 8 is a plan view of the jaw assembly at the distal end of the bipolar electrosurgical instrument illustrated in FIG. 1 taken generally along line 8—8 of FIG. 7.

FIG. 7 is a side elevation view of the distal end portion of the bipolar electrosurgical instrument 10. In FIG. 7, tissue slot 50 is clearly visible with upper ramped surface 81 and lower ramped surface 83 leading into tissue slot 50. One side of tissue separator 40, including leading edge 42 and first wedge wall 44 is visible in FIG. 7. FIG. 8 is a plan view of the distal end of the bipolar electrosurgical instrument 10 taken generally along line 8—8 of FIG. 7. First electrode wire 26 and first electrical conductor 27 extend from jaw assembly 16 through extender tube 14 and handle 12 to power cord 18.

Figure 9:
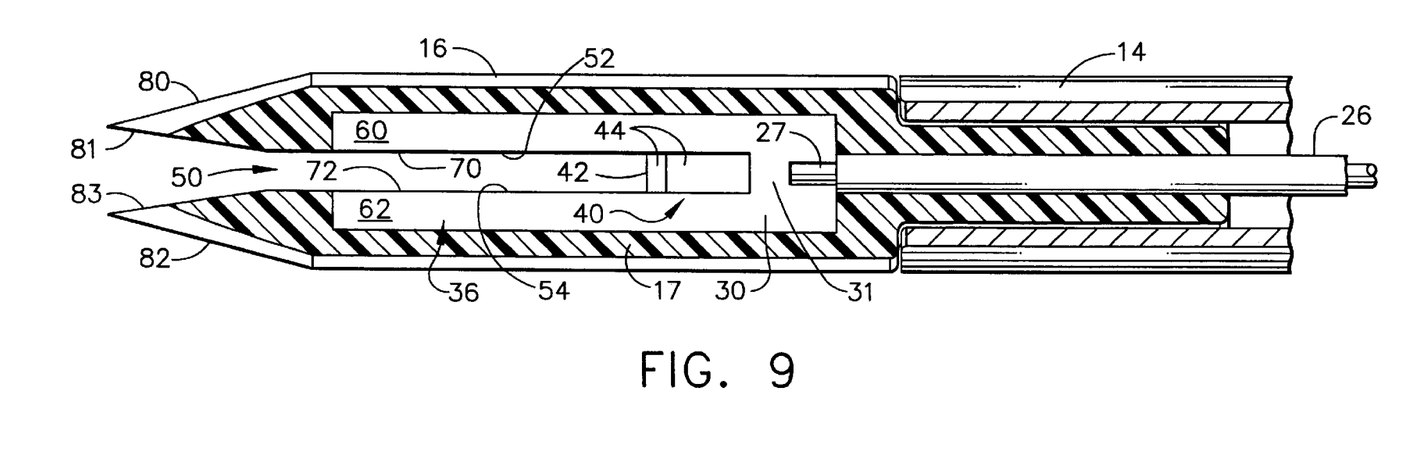
FIG. 9 is a section view in upright disposition of the jaw assembly at the distal end of the bipolar electrosurgical instrument illustrated in FIG. 1 taken generally along line 9—9 of FIG. 8.
Figure 10:
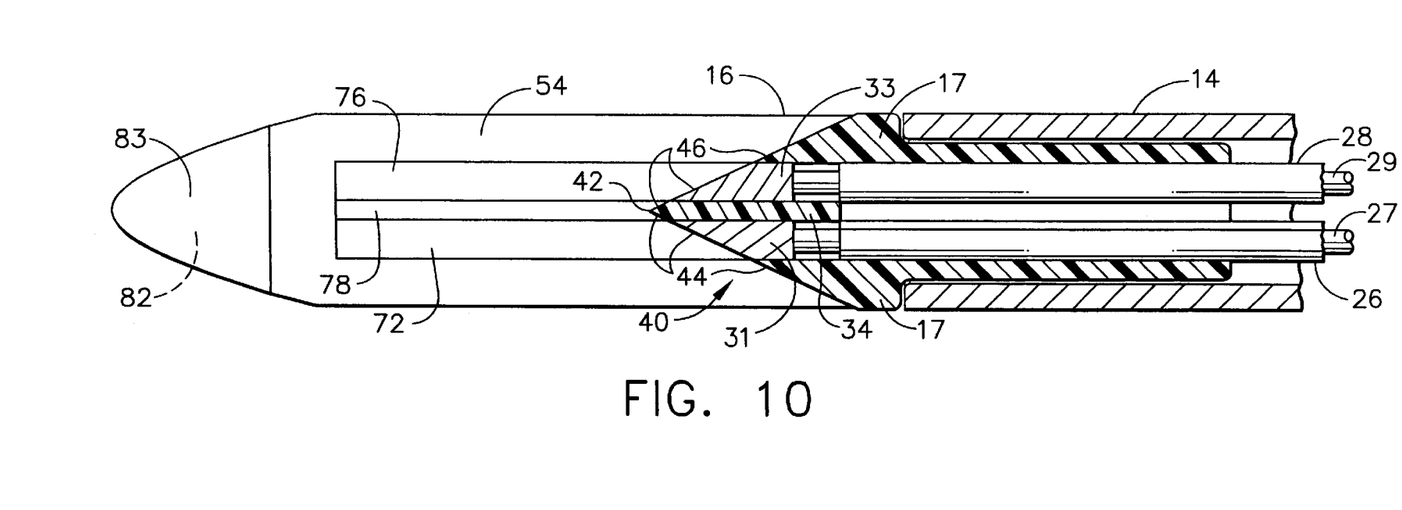
FIG. 10 is a section view in horizontal disposition of the jaw assembly at the distal end of the bipolar electrosurgical instrument illustrated in FIG. 1 taken along line 10—10 of FIG. 7.

FIG. 9 is a section view in upright disposition of the distal end of bipolar electrosurgical instrument 10 taken generally along line 9—9 of FIG. 8. As illustrated in FIG. 9, end effector 36 is embedded in insulating shell 17 with contact surface 70 and contact surface 72 forming at least a portion of first tissue surface 52 and second tissue surface 54 while first electrical wire 26 extends through insulating shell 17 and into extender tube 14. FIG. 10 is a section view in horizontal disposition of the distal end of the bipolar electrosurgical instrument illustrated in FIG. 1 taken along line 10—10 of FIG. 7. In FIG. 10, tissue separator 40 includes leading edge 42, first wall 44 and second wall 46. In the embodiment of the invention illustrated in FIG. 10, first wall 44 includes a portion of central insulator assembly 34, first support member 31 of first electrode assembly 30 and a portion of insulating shell 17 while second wall 46 includes a portion of central insulator assembly 34, a portion of second support member 33 of second electrode assembly 32 and a portion of insulating shell 17.

Figure 11:
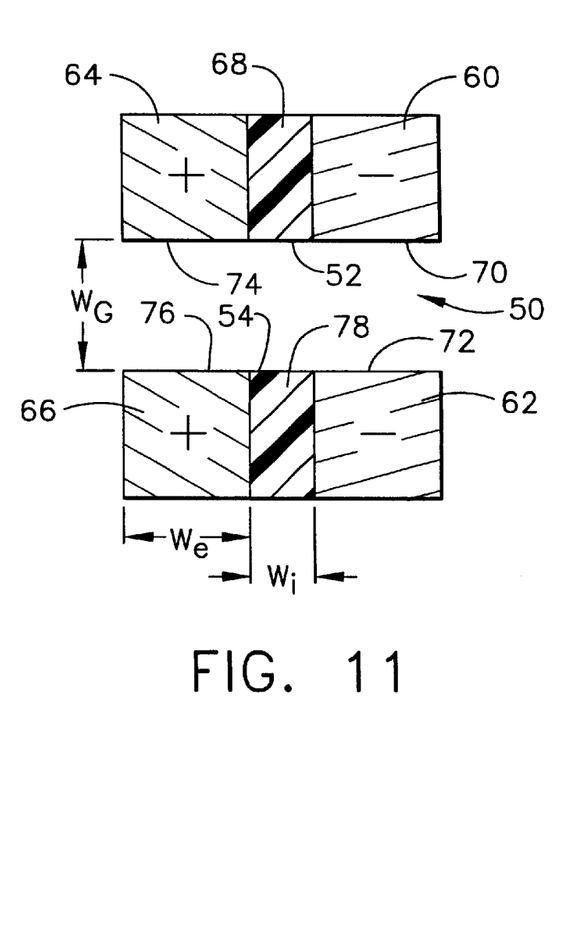
FIG. 11 is a schematic sectional view in upright disposition through the tines of the end effector illustrating the polarity and spacing of the electrode assemblies.

FIG. 11 is a schematic sectional view in upright disposition through the tines of end effector 36 illustrating the polarity and spacing of the electrode assemblies. In FIG. 11, electrodes which are electrically common are identified using the same polar markings. Thus, electrodes 64 and 66 which are electrically connected through support member 33 are both marked with a positive sign, while electrodes 60 and 62 which are electrically connected through support member 31 are both marked with a negative sign. Electrodes 64 and 66 are connected to second electric wire 28 which is connected to a first output electrosurgical generator 20 by bipolar power cord 18. Electrodes 60 and 62 are connected to second electric wire 26 which is connected to a second out put of electrosurgical generator 20 by bipolar power cord 18. Electrodes 60, 62, 64 and 66 are constructed of an electrically conductive material while central insulators 68 and 78 are constructed of material which is not electrically conductive. In the present embodiment of the invention, the working portion (i.e. the interior contact surfaces) of the end effector electrodes may be designed to be substantially C-shaped. After wires 26 and 28 are soldered to electrode assemblies 30 and 32, electrode assemblies 30 and 32 are stacked with insulator assembly 34 to form end effector 36. A wedge shaped tissue separator 40 may then be beveled into the backside of tissue slot 50 with the leading edge 42 located at the center of insulator assembly 34. Although tissue separator 40 is illustrated and described as being wedge shaped, a number of alternative-shapes would be suitable for forming tissue separator 40, including a long, thin section positioned substantially in the center of tissue slot 50. Other suitable shapes which act to separate the tissue into two parts may be apparent to those skilled in the art.

In the embodiment of the invention illustrated and described herein, there are a number of dimensions which may be adjusted to optimize the operation of the instrument for particular tissue types and particular surgical applications. In particular, as illustrated in FIG. 11, $W_G$ is the height of tissue slot 50, $W_e$ is the width of the electrode contact surface and $W_i$ is the width of the portion of central insulator assembly 34 which separates the electrode contact surfaces. More particularly, $W_i$ is the nominal distance between electrode contact surfaces 70, 74 and electrode contact surfaces 72, 76 along the length of tissue slot 50. It is important that $W_i$ be wide enough to preclude dielectric break down between the electrodes. Further, the speed at which the tissue is desiccated may be controlled by the width $W_i$, the larger $W_i$ is, the slower the instrument desiccates tissue and the smaller $W_i$ is, the faster the instrument 10 desiccates tissue down to an optimal minimum value of approximately 0.020". $W_i$ is preferably substantially constant along the length of tissue slot 50 since electrode 60 is preferably parallel to electrode 64 along the length of tissue slot 50 and electrode 62 is preferably parallel to electrode 66 along the length of tissue slot 50. Slot height $W_G$ is preferably constant along the entire length of tissue slot 50 since contact surfaces 70 and 74 are preferably parallel to contact surfaces 72 and 76 respectively along the entire length of tissue slot 50. Although a constant $W_G$ is the preferable arrangement, it may be desirable in certain circumstances to design a tissue slot 50 wherein the width of the tissue slot changes along its length, for example, it may be desirable to design a tissue slot which narrows from its distal opening to the tissue separator at its lateral end in order to increase the pressure on the treated tissue as it is moved through tissue slot 50. However, in a bipolar electrosurgical instrument according to the present invention, the instrument is designed such that the height $W_G$ at each point along the length of tissue slot 50 is generally fixed and unchanging during the time tissue is being moved through tissue slot 50 and treated. In a typical instrument according to the present invention, a preferred value for $W_G$ would be in the range of approximately 0.020"–0.030" which would be expected to provide optimal compression of blood vessels ranging in size from approximately one to four millimeters in diameter as the blood vessels are moved into and along tissue slot 50. An instrument 10 with a larger height $W_G$ will be able to accept and treat a larger range of vessels (e.g. 4–7 mm) or thicker tissue. Such blood vessels may be found in, for example, side branches of the saphenous vein which must be sealed when the saphenous vein is harvested for use in, for example, arterial bypass operations. Once tissue, such as, for example, saphenous vein side branches are inserted into tissue slot 50, electrosurgical energy may be applied to the vein side branches through electrodes 60, 64, 62 and 66. It would further be expected, for reasons discussed below, that optimal cauterization of the tissue in tissue slot 50 would occur when $W_G$ is less than twice of $W_e$. Longer tissue slot lengths may also be desirable since the more tissue engaged by the slot, the lower the total impedance and the faster the tissue cooks.

Figure 12:
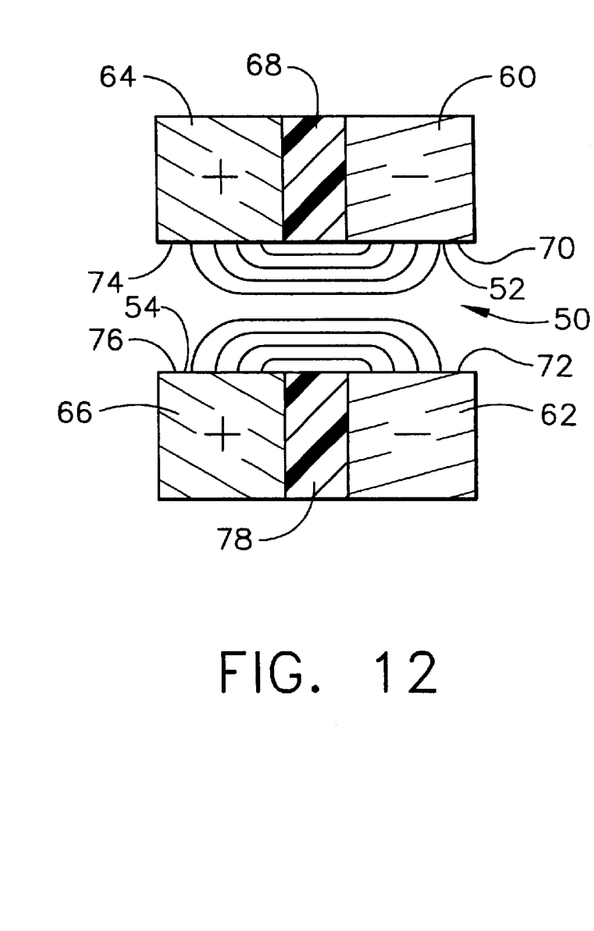
FIG. 12 is a schematic sectional view like that of FIG. 6 illustrating the primary flow paths of electrosurgical current as it passes through tissue engaged by an end effector according to the present invention.
Figure 13:
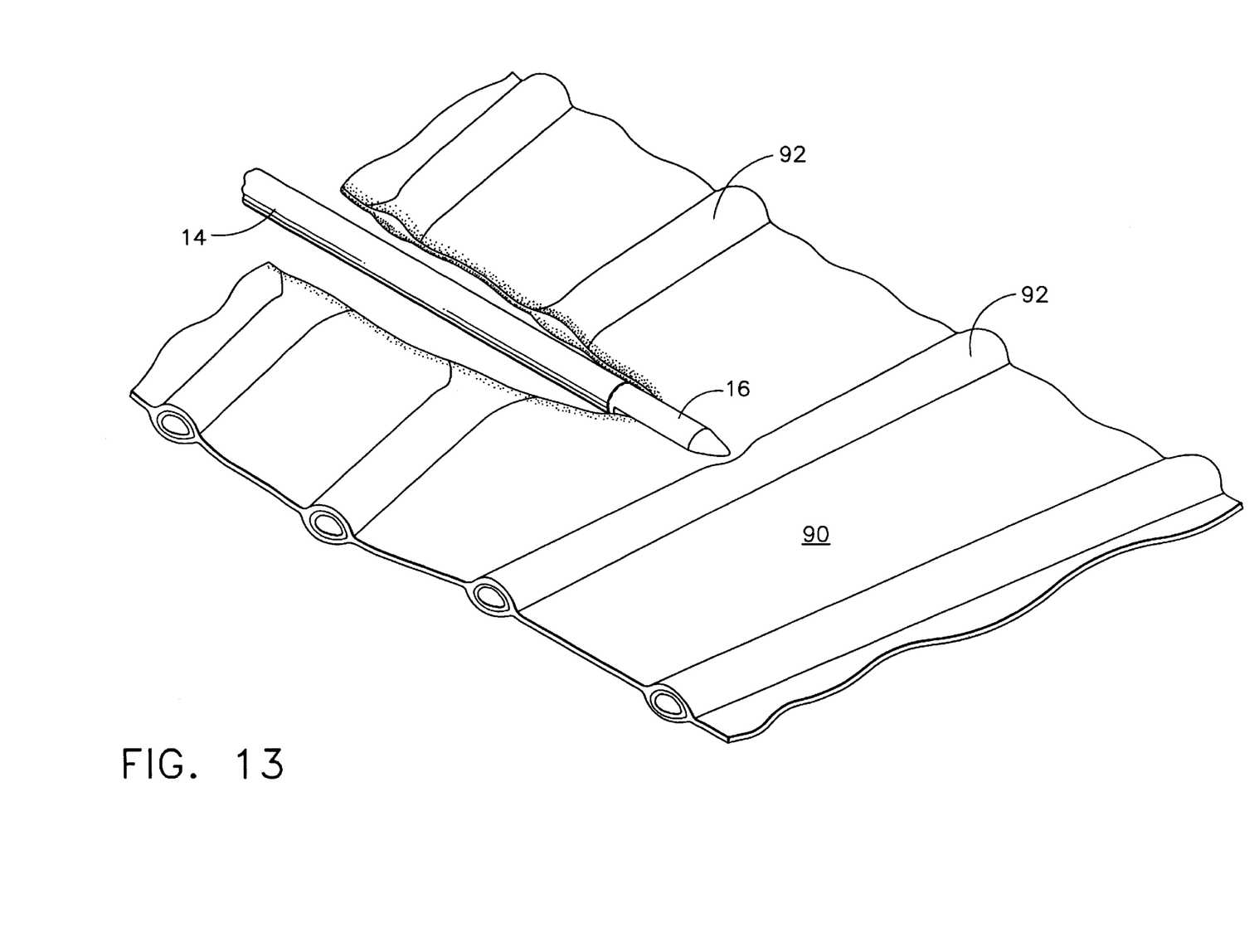
FIG. 13 is a perspective view of a surgical procedure wherein a bipolar electrosurgical instrument according to the present invention is being used to cauterizing and cut tissue and blood vessels in the mesentery during abdominal surgery.

FIG. 12 is a schematic sectional view like that of FIG. 11 illustrating the primary flow paths electrosurgical current takes as it passes through tissue engaged by jaw assembly 16 of bipolar electrosurgical instrument 10. Typical current pathways are shown in FIG. 12. FIG. 13 is a perspective view of a surgical procedure wherein a bipolar electrosurgical instrument 10 according to the present invention is being used to cauterizing and cut mesentery tissue 90, including blood vessels 92 in the mesentery tissue, during abdominal surgery.

In operation, tissue, such as mesentery tissue 90, is inserted by a surgeon into the distal end of tissue slot 50. Tissue is guided into tissue slot 50 by upper ramped surface 81 and lower ramped surface 83 while upper dissector 80 and lower dissector 82 serve to guide surrounding tissue away from tissue slot 50, dissecting the tissue being treated from the surrounding tissue and preventing the surrounding tissue from being forced into tissue slot 50. As tissue is forced into tissue slot 50, the surgeon will supply electrosurgical energy to electrodes 60, 62, 64 and 66 by, for example, activating electrosurgical generator 20 using, for example foot switch 22. When electrosurgical generator 20 is activated, it generates an alternating electrical potential at electrodes 60, 62, 64, and 66. As illustrated in FIG. 11, the instantaneous electric potential at electrode 64 is the same as the instantaneous electric potential at electrode 66, while the instantaneous electric potential at electrode 60 is the same as the instantaneous electric potential at electrode 62. Electrodes 60 and 62 have a an instantaneous electric potential which differs from and is generally of the same magnitude and opposite polarity as the electric potential applied to electrodes 64 and 66. Thus, since a potential voltage is generated between electrodes of different electrical potentials, when an electrically conductive material, such as tissue, is placed in contact with both contact surface 70 and contact surface 74 electric current will flow between electrode 60 and electrode 64. Likewise, when an electrically conductive material, such as tissue, is placed in contact with both contact surface 72 and contact surface 76, electric current will flow between electrode 62 and electrode 66. However, since electric current seeks the path of least resistance, which, all other variables being constant, is the shortest path, current traveling through tissue in tissue slot 50 will tend to travel in a first primary path between contact surface 70 and contact surface 74 and in a second primary path between contact surface 72 and contact surface 76 as illustrated in FIG. 12. Although current will flow in other alternative pathways, the primary initial current pathways in an end effector 36 according to the present invention will be those illustrated in FIG. 12. Further, since the shortest pathway through tissue in tissue slot 50 is along the region adjacent the surface of the tissue, initially the current density will be highest in the region along and just below the surface of the tissue. As the tissue adjacent the top and bottom of tissue slot 50 begins to heat and desiccate, its electrical resistance increases and the primary current pathways are driven deeper and deeper into the tissue, toward the midpoint between first tissue surface 52 and second tissue surface 54. This process is enhanced by the pressure on the tissue in tissue slot 50 which forces fluids, including water and blood, out of the tissue as it is forced into tissue slot 50 and which acts to facilitate coagulation and sealing of blood vessels inserted into tissue slot 50. Tissue slot 50 is designed to receive the tissue to be treated while generating considerable pressure on that tissue as it is fed into tissue slot 50. An end effector 36 according to the present invention is also beneficial in that the current through the tissue tends to be self-limiting.

Once the tissue is adequately desiccated, the current flow will be reduced or eliminated, eliminating the power transfer, and thus the resistive heating in the tissue. In an end effector according to the present invention, the tissue in tissue slot 50 will become desiccated very quickly and the tissue reaching tissue separator 40 will generally be fully desiccated and any blood vessels in the tissue will be sealed on both sides of tissue slot 50. Thus, as the treated tissue passes the tip of tissue separator 40, it will be separated into two parts by leading edge 42 and guided out of tissue slot 50 by first wedge wall 44 and second wedge wall 46.

In a more general sense, a bipolar electrosurgical instrument according to the present invention works by using resistive heating to cook the tissue vertically from the outer edges toward the center of the tissue and laterally working from the central portion out toward the edges of tissue slot 50 as the tissue moves continuously through tissue slot 50. As tissue near the top and bottom of tissue slot 50 and between insulators 68 and 78 begins to heat, the resistance of the tissue in the treated region goes up and current is shunted to other paths with lower resistance. Thus, the current density drops off in the original volume of tissue and increases in the lower resistance regions, causing those regions to heat up. This process continues until the tissue is thoroughly treated and the resistance increases throughout the treated region. As the tissue resistance increases, the impedance load seen by the electrosurgical generator increases and the load represented by the tissue becomes mismatched with the output of the generator. With a significant load mismatch little or no additional energy is dissipated in the tissue.

An end effector 36 according to the present invention is particularly beneficial since it means that the most critical region, that is the region in the center of tissue slot 50 through which leading edge 42 passes, is the first region treated and the region that is treated most thoroughly. More particularly, by insuring that the height $W_G$ of tissue slot 50 is less than 2 times the electrode width $W_e$, the tissue in the middle of tissue slot 50 is cooked first and efficiently. Further, since the current in an end effector 36 according to the present invention is self-limiting, there is little or no thermal damage to the tissue outside of jaw assembly 16 and the thermal damage is limited to the region necessary to ensure that the tissue on both sides of the cut line is adequately coagulated and sealed. Further, since the transfer of energy to the tissue engaged by end effector 36 is self regulating, the surgeon may continue to apply energy to the instrument and may move the instrument laterally through the tissue at a speed convenient to the surgeon without substantial lateral thermal damage to the tissue surrounding jaw assembly 16. The surgeon may even stop the movement of the instrument through the tissue while continuing to activate electrosurgical generator 20 and the current to the tissue will self-limit after the tissue within end effector 36 is treated with little or no lateral thermal damage to the tissue outside jaw assembly 16. In particular, the lateral thermal damage caused by the thermal conduction from the coagulated tissue would be expected to be typically on the order of 0.5 to 1 mm outside of jaw assembly 16. As an additional benefit, because the use of the instrument is not technique sensitive, for the reasons set forth above, different surgeons using the instrument in similar tissue are likely to see substantially similar results.

Bipolar electrosurgical instruments incorporating end effectors according to the present invention are particularly adapted for use in sealing and cutting individual blood vessels. Although blood vessels are generally tough, the breakdown of collagen by electrosurgical energy and the pressure of being forced through tissue slot 50 will make the vessel tissue significantly weaker than normal, making it easy to mechanically ligate the treated vessel using tissue separator 40. Thus, using an end effector 36 according to the present invention, a blood vessel inserted into tissue slot 50 is compressed and coagulated in a single step, sealing the vessel to prevent it from leaking when it is cut. The vessel is then divided in the middle of the coagulated region, leaving two sealed ends behind, reducing or eliminating the need to use two or more mechanical clips to seal the vessel before it is cut. It may further be advantageous to use a tissue separator 40 which includes a surgically dull leading edge 42 since a surgically dull tissue separator will not cut healthy tissue as it is inserted into the tissue slot, thus preventing healthy tissue from being cut inadvertently as it is fed into the tissue slot prior to the application of electrosurgical energy by the surgeon. Once the tissue in the slot has been electrosurgically treated, it is desiccated and my be readily divided by tissue separator 40.

It will be recognized that equivalent structures may be substituted for the structures illustrated and described herein and that the described embodiment of the invention is not the only structure which may be employed to implement the claimed invention. As one example of an equivalent structure which may be used to implement the present invention, jaw assembly 16 could be formed from an electrically nonconductive material with electrodes 60, 62, 64 and 66 comprising an electrically conductive material deposited on the inner surface of tissue slot 50 and connected by electrical conductors, such as wires, to first electrical wire 26 and second electrical wire 28. As a further example, one or more of electrodes 60, 62, 64 and 66 may comprise a plurality of electrically conductive regions or surfaces arranged along the interior tissue slot 50 to form electrode regions which cover substantially the same area on the interior surfaces of tissue slot 50 as the electrodes described and illustrated herein. As a further example, one or more of electrodes 60, 62, 64 and 66 may include a spring mechanism adapted to force the contact surfaces 70, 72, 74 and 76 against tissue positioned in tissue slot 50 to improve contact between tissue in slot 50. A further embodiment of the present invention may only include first electrode 60 and second electrode 62 with the second tissue surface not including any electrodes and being constructed of, for example, a nonconductive material.

It will be understood that the tissue effects of the present invention have not been fully characterized. It is believed that tissue in the center of the tissue slot will be fully desiccated as a result of the electrical current passing between the electrodes. Since the temperature gradient decreases in tissue away from the center of the tissue slot, tissue on either side of the center will be more likely to be coagulated and not reach total desiccation. It is further believed that steam generated in the central tissue will assist in fracturing that tissue, facilitating transaction by the tissue separator.

While preferred embodiments of the present invention have been shown and described herein, it will be obvious to those skilled in the art that such embodiments are provided by way of example only. Numerous variations, changes, and substitutions will now occur to those skilled in the art without departing from the invention. Accordingly, it is intended that the invention be limited only by the spirit and scope of the appended claims.

What is claimed is:

1. A bipolar end effector comprising:
   a first tissue surface, wherein said first tissue surface comprises a first and a second side;
   a second tissue surface separated from said first tissue surface by a tissue slot, said tissue slot being defined by a distance between said first tissue surface and said second tissue surface, wherein said distance is fixed;
   a plurality of elongated electrodes, wherein said elongated electrodes are located on at least one of said tissue surfaces and are electrically isolated from each other;

a tissue separator positioned between said first and said second tissue surfaces, wherein said tissue separator comprises;

a dividing edge at the distal end of said tissue separator;

a first tissue guide extending proximally away from said dividing edge toward said first side; and a second tissue guide extending proximally away from said dividing edge toward said second side.

2. A bipolar end effector according to claim 1 wherein said bipolar end effector further comprises;

a first elongated electrode from said plurality of elongated electrodes on said first side of said first tissue surface;

a second elongated electrode from said plurality of elongated electrodes on said second side of said first tissue surface, wherein said second elongated electrode is substantially parallel to said first electrode; and a first insulated region separating said first elongated electrode from said second elongated electrode.

3. A bipolar end effector according to claim 2 wherein said bipolar end effector further comprises;

a third elongated electrode from said plurality of elongated electrodes on a first side of said second tissue surface;

a fourth elongated electrode from said plurality of elongated electrodes on a second side of said second tissue surface, wherein said fourth elongated electrode is substantially parallel to said third elongated electrode; and a second central insulation region separating said third electrode from said fourth electrode.

4. A bipolar end effector according to claim 3 wherein;

Said first and third elongated electrodes are electrically connected and

Said second and fourth elongated electrodes are electrically connected.

5. A bipolar end effector according to claim 3 wherein said first elongated electrode is positioned substantially directly opposite said third elongated electrode and said second elongated electrode is positioned substantially opposite said fourth elongated electrode.

6. A bipolar end effector according to claim 1 wherein said tissue separator further comprises a wedge shaped region.

7. A bipolar end effector according to claim 1 wherein said dividing edge is surgically dull.

8. A bipolar end effector according to claim 1 wherein said distance is substantially constant along the length of said tissue slot.

9. A bipolar end effector according to claim 1 wherein said distance at the distal end of said tissue slot is larger than the said distance at the proximal end of said tissue slot.

* * * * *